United States Patent [19]

Sequeira et al.

[11] Patent Number: 4,775,529

[45] Date of Patent: Oct. 4, 1988

[54] STEROID LOTION

[75] Inventors: Joel A. Sequeira, New York, N.Y.; Farah J. Munayyer, West Caldwell; Rebecca Galeos, Bloomfield, both of N.J.

[73] Assignee: Schering Corporation, Kenilworth, N.J.

[21] Appl. No.: 53,172

[22] Filed: May 21, 1987

[51] Int. Cl.[4] .................. A61K 31/57; A61K 31/78; A61K 47/00
[52] U.S. Cl. .................................... 424/81; 514/171; 514/174; 514/179; 514/180
[58] Field of Search ............... 514/171, 174, 177, 180; 424/81

[56] References Cited

U.S. PATENT DOCUMENTS

| | | | |
|---|---|---|---|
| 2,890,152 | 6/1959 | Babcock et al. | 514/171 |
| 3,352,752 | 11/1967 | Lerner | 514/174 |
| 3,592,930 | 7/1971 | Katz et al. | 514/174 |
| 3,711,606 | 1/1973 | Herschler | 514/174 |
| 3,749,773 | 7/1973 | Ninger et al. | 514/944 |
| 3,758,686 | 9/1973 | Sieger et al. | 514/174 |
| 3,856,954 | 12/1974 | Jackson | 514/174 |
| 3,892,857 | 1/1975 | Difazio et al. | 514/174 |
| 4,013,792 | 3/1977 | Eichman et al. | 514/171 |
| 4,185,100 | 1/1980 | Rover et al. | 514/171 |
| 4,654,209 | 3/1987 | Leslig et al. | 514/174 |

*Primary Examiner*—Shep K. Rose
*Attorney, Agent, or Firm*—John J. Maitner; Stephen I. Miller; James R. Nelson

[57] ABSTRACT

An improved lotion formulation for the topical administration of corticosteroids in a hydro-alcoholic base containing propylene glycol.

18 Claims, No Drawings

STEROID LOTION

This invention relates to a topical lotion for use in the application of steroid medicaments. More particularly, this invention relates to an improved lotion vehicle for steroids having improved properties.

The present invention provides a corticosteroid lotion formulation exhibiting high vasoconstrictor activity and excellent anti-inflammatory activity in steroid responsive dermatoses. The addition of propylene glycol to a hydro-alcoholic lotion base exhibits significantly higher vasoconstrictor activity than the corresponding lotion without propylene glycol. This increase in vasoconstrictor activity appears to be unique to propylene glycol since substitution of propylene glycol with another glycol, such as hexylene glycol or polyethylene glycol 400, decreases the vasoconstrictor activity of the lotion formulation.

This present invention comprises a topical composition for the treatment of dermatological disorders that are responsive to corticosteroids. The topical composition comprises an amount effective to treat an inflammation of a dermatologically acceptable anti-inflammatory corticosteroid in a hydro-alcoholic base comprising:

(a) 15 to 50% by weight propylene glycol
(b) 20 to 40% by weight isopropyl alcohol
(c) 20 to 60% by weight water
(d) 0.1 to 3.0% by weight of a thickening agent
(e) sufficient buffer to adjust the pH to between 3.0 to 6.0.

This invention particularly relates to topical lotions which contain a steroid anti-inflammatory agent as the active ingredient and to a method of treating inflammatory conditions in patients by administering these lotions. The anti-inflammatory agents disclosed herein are of value in the topical treatment of dermatological disorders or like conditions responsive to anti-inflammatory drugs. Included in this category are disorders such as psoriasis, seborrheic dermatitis, atopic dermatitis, contact dermatitis and eczema.

Treatment with the lotions of this invention is usually accomplished by applying the lotion to completely cover the affected area. The usual frequency of application is two to three times daily, although adequate maintenance therapy for some patients may be with less frequent application.

The lotion of the present invention comprises a therapeutically effective amount of dermatologically acceptable anti-inflammatory corticosteroid. The therapeutically effective amount of corticosteroid is generally an amount of from 0.01 to 1.0% by weight of the total composition. Ranges of 0.02 to 0.2% are particularly suitable with a range of 0.05 to 0.1% by weight being most preferable.

The particular steroid medicaments useful in the composition of the present invention are dermatologically acceptable anti-inflammatory corticosteroids. Examples of corticosteroids are betamethasone 17,21-dipropionate, alclometasone dipropionate, mometasone furoate [9α,21-dichloro-16α-methyl-1,4-pregnadiene-11β,17α-diol-3,20-dione-17-(2-furoate)], fluocinonide, halcinonide and desoximetasone.

This lotion composition of the present invention may contain a thickening agent to achieve a lotion consistency. Examples of thickening agents useful in the invention are: Carbomer 940, an acrylic acid polymer having an approximate molecular weight of 4,000,000 and available from B. F. Goodrich Chemical Company; Klucel ®, hydroxypropyl cellulose which is a propylene glycol ether of cellulose available from Hercules Inc., Methocel ® A, methyl cellulose which is a methyl ether of cellulose available from Dow Chemicals; and Polyquaternium-10 which is a polymeric quaternary ammonium salt of hydroxyethyl cellulose reacted with a trimethyl ammonium substituted epoxide, available from Amerchol Corp. Cosmetic preference or stability considerations will dictate selection of the thickening agent.

The pH of the lotion composition of the present invention is generally in the range of about 3.0 to 6.0 and preferably pH 4 to 5. Sufficient buffer solution is added to the lotion composition to maintain the pH in the desired range. Examples of buffers useful in the present invention are phosphate buffer, citrate buffer, citrate-phosphate buffer.

The lotion of the present invention is manufactured in a conventional manner by thoroughly mixing the ingredients at ambient or elevated temperatures in order to achieve solubility of ingredients where appropriate.

The following formulation examples illustrate the lotion compositions of the invention. It will be apparent to those skilled in the art that many modifications thereof may be practical without departing from the purpose and intent of this disclosure. The definition of components whose chemical composition is not immediately clear from the name used may be found in the CTFA Cosmetic Ingredients Dictionary, 3rd Edition, published by Cosmetic Toiletry and Fragrance Association, Inc., Washington, D.C.

EXAMPLE 1

A topical 0.05% betamethasone dipropionate topical lotion formulation in accordance with the present invention having the following composition:

| Ingredients | mg/g |
| --- | --- |
| Betamethasone Dipropionate USP | 0.64* |
| Sodium Phosphate Monobasic Monohydrate R | 2.00 |
| Phosphoric Acid NF | ** |
| Sodium Hydroxide R | ** |
| Propylene Glycol USP | 300.00 |
| Isopropyl Alcohol USP | 300.00 |
| Hydroxypropyl Cellulose NF | 1.50 |
| Purified Water USP q.s. | 1.00 g |

*Equivalent to 0.5 mg Betamethasone/g
**Used to adjust the pH to 4.5 ± 0.2

In preparing the topical lotion formulation, the steroid is dissolved in isopropyl alcohol. Hydroxypropylcellulose is dispersed in the alcohol solution. A solution of sodium phosphate monobasic in water is added to the isopropyl alcohol solution. Propylene glycol is then added and the solution is adjusted to total weight. Phosphoric acid is used to adjust the lotion to the target pH. In case the thickening agent is Carbomer 940, sodium hydroxide is added to neutralize the acidic pH of the lotion and to achieve a final pH of approximately 4.5.

EXAMPLE 2

A 0.05% alclometasone dipropionate lotion formulation in accordance with the present invention having the following composition.

| Ingredients | mg/g |
| --- | --- |
| Alclometasone dipropionate | 0.5 |
| Carbomer 940 | 2.60 |
| Sodium Hydroxide, R | 0.04 |
| Propylene Glycol, USP | 200.0 |
| Isopropyl Alcohol, NF | 300.0 |
| Hydrochloric Acid | * |
| Purified Water, USP q.s. ad to | 1.0 g |

*Used to adjust the pH to 4.5

EXAMPLE 3

A 0.1% mometasone furoate lotion formulation in accordance with the present invention having the following composition:

| Ingredients | mg/g |
| --- | --- |
| Mometasone furoate | 1.0 |
| Alcohol Isopropyl USP | 400.0 |
| Propylene Glycol USP | 300.0 |
| Hydroxypropylcellulose (Klucel HF) | 1.5 |
| Sodium Phosphate Monobasic Monohydrate R | 2.0 |
| Phosphoric Acid NF | * |
| Water Purified USP q.s. to make | 1 g |

*Used to adjust the pH to 4.5 ± 0.1.

EXAMPLE 4

A 0.05% fluocinonide lotion formulation in accordance with the present invention having the following composition:

| Ingredients | mg/g |
| --- | --- |
| Fluocinonide | 0.50 |
| Sodium Phosphate Monobasic Monohydrate R | 2.00 |
| Phosphoric Acid NF | * |
| Sodium Hydroxide R | * |
| Propylene Glycol USP | 300.00 |
| Isopropyl Alcohol USP | 300.00 |
| Hydroxypropyl Cellulose NF | 1.50 |
| Purified Water USP q.s. | 1.00 g |

*Used to adjust the pH to 4.5

EXAMPLE 5

A 0.1% halcinonide lotion formulation in accordance with the present invention having the following composition:

| Ingredients | mg/g |
| --- | --- |
| Halcinonide | 1.00 |
| Sodium Phosphate Monobasic Monohydrate R | 2.00 |
| Phosphoric Acid NF | * |
| Sodium Hydroxide R | * |
| Propylene Glycol USP | 300.00 |
| Isopropyl Alcohol USP | 300.00 |
| Hydroxypropyl Cellulose NF | 1.50 |
| Purified Water USP q.s. | 1.00 g |

*Used to adjust the pH to 4.5

EXAMPLE 6

A 0.05% desoximetasone lotion formulation in accordance with the present invention having the following composition:

| Ingredient | mg/g |
| --- | --- |
| Desoximetasone | 0.50 |
| Sodium Phosphate Monobasic Monohydrate R | 2.00 |
| Phosphoric Acid NF | * |
| Sodium Hydroxide R | * |
| Propylene Glycol USP | 300.00 |
| Isopropyl Alcohol USP | 300.00 |
| Hydroxypropyl Cellulose NF | 1.50 |
| Purified Water USP q.s. | 1.00 g |

*Used to adjust the pH to 4.5

Local anti-inflammatory activity of the topical compositions of this invention were tested by the vasconstrictor assay described by McKenzie and Stoughton, Arch. Dermatol., 86, 608 (1962)

Sixteen to 32 subjects from a pool of healthy volunteers who met certin selection criteria were selected for each study. No individual was used more frequently than once every two weeks.

Four sites, each approximately 2 cm in diameter and at least 1 cm apart, were delineated on the flexor surface of each of the subject's forearms, giving a total number of eight sites per subject. Ten (10) mg of each of the formulations tested per study were randomnly applied to these sites using a Latin square design code, so that each site location received each test preparation an equal number of times.

The four sites on each arm were then covered with a protective plastic shield. Six and one half hours later the shields were removed, and the test sites were washed with soap and water. Approximately ½ and 18 hours after removal of the shields, (7 and 24 hours after initial application of the test materials), the sites were examined and the degree of blanching (vasoconstriction) was graded as follows: No blanching—0; mild blanching—1; moderate blancing—2 and strong blancing—3.

Table I reports the results of a topical composition of this invention containing propylene glycol with a corresponding formulation without propylene glycol. In two test panels of 24–32 subjects per panel, the lotion with propylene glycol exhibits significantly higher vasoconstrictor activity than the lotion without propylene glycol. BDP represents betamethasone dipropionate.

TABLE I

| VASOCONSTRICTOR ACTIVITY OF STEROID LOTIONS | | |
| --- | --- | --- |
| | VASCOCONSTRICTOR SCORE AT 7 HOURS | |
| LOTION | TEST 1 | TEST 2 |
| BDP Lotion, 0.05% with propylene glycol | 1.8 | 1.5 |
| BDP Lotion, 0.05% without propylene glycol | 1.5 | 1.1 |

Table II reports data demonstrating that when another glycol, such as hexylene glycol or polyethylene glycol 400, is replaced for propylene glycol, the vasconstrictor activity of the propylene glycol formulation, is significantly higher than the other two glycol containing formula.

TABLE II

| | VASOCONSTRICTOR SCORE | |
| --- | --- | --- |
| LOTION | 7 HOURS | 24 HOURS |
| BDP Lotion, 0.05% with propylene glycol | 1.5 | 0.6 |
| BDP Lotion, 0.05% with hexylene glycol | 0.7 | 0.4 |
| BDP Lotion, 0.05% | 0.2 | 0.1 |

TABLE II-continued

| LOTION | VASOCONSTRICTOR SCORE | |
|---|---|---|
| | 7 HOURS | 24 HOURS |
| with PEG 400 | | |

Table III reports data of a 0.05% alclometasone lotion containing propylene glycol. Substituting propylene glycol with another glycol, hexylene glycol, caused a significant decrease in vasconstrictor activity. AD represents alclometasone dipropionate.

TABLE III

VASOCONSTRICTOR ACTIVITY OF ALCLOMETASONE DIPROPIONATE (AD) LOTIONS

| LOTION | VASOCONSTRICTOR ACTIVITY | |
|---|---|---|
| | 7 HOURS | 24 HOURS |
| AD Lotion, 0.05% with 20% propylene glycol | 1.1 | 0.16 |
| AD Lotion, 0.05% with 20% hexylene glycol | 0.41 | 0.09 |

The data presented in foregoing tables demonstrate that propylene glycol uniquely potentiates the vasconstrictor activity and anti-inflammatory activity of steroids when formulated in a hydro-alcoholic base of this invention.

What is claimed is:

1. A topical lotion for the treatment of inflammation which comprises an amount effect to treat said inflammation of a dermatologically acceptable anti-inflammatory corticosteroid in a hydro-alcoholic base consisting essentially of:
   15 to 50% by weight of propylene glycol;
   20 to 40% by weight of isopropyl alcohol;
   20 to 60% by weight water;
   0.1 to 3.0% by weight of a thickening agent, and sufficient buffer to maintain the pH of the composition within the range of 3.0 to 6.0.

2. The lotion of claim 1 wherein the corticosteroid comprises 0.01 to 1.0% by weight of the composition.

3. The lotion of claim 2 wherein the corticosteroid comprises 0.02 to 0.2% by weight of the composition.

4. The lotion of claim 1 wherein the corticosteroid is betamethasone 17,21-dipropionate.

5. The lotion of claim 4 wherein the betamethasone 17,21-dipropionate is present in an amount of 0.064% by weight.

6. The lotion of claim 5 consisting essentially of:

| Ingredients | Concentration (mg/g) |
|---|---|
| Betamethasone Dipropionate USP | 0.64* |
| Sodium Phosphate Monobasic Monohydrate R | 2.00 |
| Phosphoric Acid NF | ** |
| Sodium Hydroxide R | ** |
| Propylene Glycol USP | 300.00 |
| Isopropyl Alcohol USP | 300.00 |
| Hydroxypropyl Cellulose NF | 1.50 |
| Purified Water USP q.s. | 1.00 g |

*Equivalent to 0.5 mg Betamethasone/g
**Used to adjust the pH to 4.5 ± 0.2

7. The lotion of claim 1 wherein the corticosteroid is alclometasone dipropionate.

8. The lotion of claim 7 consisting essentially of:

| Ingredients | Concentration mg/g |
|---|---|
| Alclometasone Dipropionate | 0.5 |
| Carbomer 940 | 2.60 |
| Sodium Hydroxide, R | 0.04 |
| Propylene Gylcol, USP | 200.0 |
| Isopropyl Alcohol, NF | 300.0 |
| Hydrochloric Acid | * |
| Purified Water, USP q.s. ad to | 1.0 g |

*Used to adjust the pH to 4.5

9. The lotion of claim 1 wherein the corticosteroid is mometasone furoate.

10. The lotion of claim 9 consisting essentially of:

| Ingredients | Concentration mg/g |
|---|---|
| Mometasone Furoate | 1.0 |
| Alcohol Isopropyl USP | 400.0 |
| Propylene Glycol USP | 300.0 |
| Hydroxypropyl Cellulose (Klucel HF) | 1.5 |
| Sodium Phosphate Monobasic Monohydrate R | 2.0 |
| Phosphoric Acid NF | * |
| Water Purified USP q.s. | 1 g |

*Used to adjust the pH to 4.5 ± 0.1

11. The lotion of claim 1 wherein the thickening agent is an acrylic acid polymer.

12. The lotion of claim 1 wherein the thickening agent is hydroxypropyl cellulose.

13. The method of treating inflammation which comprises applying to the skin a topical lotion formulation comprising an amount effective to treat said inflammation of a dermatologically acceptable anti-inflamatory corticosteroid in a hydro-alcoholic base consisting essentially of:
   15 to 50% by weight of propylene glycol;
   20 to 40% by weight of isopropyl alcohol;
   20 to 60% by weight water;
   0.1 to 3.0% by weight of a thickening agent, and sufficient buffer to maintain the pH of the composition within the range of 3.0 to 6.0.

14. The method of claim 13 wherein the corticosteroid comprises 0.01 to 1.0% by weight of the composition.

15. The method of claim 14 wherein the corticosteroid comprises 0.02 to 0.2% by weight of the composition.

16. The method of claim 13 wherein the corticosteroid is betamethasone 17,21-dipropionate.

17. The method of claim 13 wherein the corticosteroid is alclometasone dipropionate.

18. The method of claim 13 wherein the corticosteroid is mometasone furoate.

* * * * *